United States Patent [19]

Schelbeck

[11] Patent Number: Plant 5,391

[45] Date of Patent: Jan. 15, 1985

[54] BEGONIA PLANT NAMED ELLEN

[75] Inventor: Erland V. Schelbeck, Odense, Denmark

[73] Assignee: L. Daehnfeldt Ltd., Odense, Denmark

[21] Appl. No.: 506,213

[22] Filed: Jun. 20, 1983

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of begonia named Ellen characterized by its large flower size and compound inflorescence, brilliant and uniform red flower color, fast propagation, rapid flowering, and its foliage which is infused with maroon in margins and underside.

1 Drawing Figure

The present invention relates to a new and distinctive cultivar of begonia plant, obtanically known as *Begonia hiemalis* (Fotsch) and known by the cultivar name Ellen.

The new cultivar was discovered by me in Odense, Denmark as a seedling from a controlled crossing of tuberous hybrida seedling P 156 as the seed parent with begonia Socotrana as the pollen parent.

Asexual reproduction by me in Odense, Denmark by stem and/or leaf cuttings has reproduced the unique features of the new cultivar through successive propagations.

The following characteristics distinguish the new begonia from both its parent and other begonias commercially known and used in the floriculture industry:

1. The flower size of Ellen is larger than the cultivar Dorthe, disclosed in applicant's pending application Ser. No. 420,521. Quite often the flowers of Ellen are compound with several, up to as many as 8, centers as illustrated in the upper right hand flower in the photographic drawing. This compound inflorescence also appears in the cultivar Ninon, disclosed in my pending application Ser. No. 420,522.

2. The foliage of Ellen is larger, more serrated, and the apex more pointed than the foliage of Dorthe.

3. The new cultivar propagates extremely fast and uniform by leaf cuttings, propagation more similar to Connie, disclosed in my pending application Ser. No. 420,500, than Dorthe.

4. Flowering is rapid, someimes causing problems of crop planning unless propagating stock and young plants are kept vegetative by high light and above normal nutrition.

5. Flower color is the most brilliant red known to date in commercial hiemalis begonias, being a more brilliant red rather than the somewhat tinted red of Dorthe.

6. Ellen is less susceptible to flower bud drop in the winter months than Connie or Dorthe and the cultivars with double flowers introduced by other hybridizers.

7. Ellen can be produced with excellent quality in 10 to 14 cm. pots year round.

8. Foliage is infused with maroon, especially in the margins and underside.

9. Compact growth habit, with rigid and vigorous stems.

10. Foliage and flowers are in nice proportions to present excellent display.

11. Flower color is very uniform throughout blooming period, with very little fading. Flower color is unusually uniform from top side to bottom side of tepals.

The accompanying colored photograph taken in April 1983 illustrates in perspective the overall appearance of Ellen grown in a 10 cm. plastic pot, and shows the colors as true as it is reasonably possible to obtain in a colored reproduction of this type.

The following is detailed description of my new begonia cultivar based on plants produced under commercial practices in Odense, Denmark and Ashtabula, Ohio. Color references are made to The Royal Horticultural Society Colour Chart except where general color terms of ordinary dictionary significance are used.

PARENTAGE

Seed parent tuberous hybrida seedling P156 crossed with species socotrana.

PROPAGATION

Type cutting: Tip or shoot cuttings 2–3 cm. long.

Time to root to planting: 24–28 days at 21°–22° C. summer; 30–35 days at 19°–20° C. winter.

Rooting habit: Abundant, fibrous. When propagating by leaf cuttings, rooting and shooting are extremely fast and abundant in both summer (within 60 days) and winter (within 75 days).

PLANT DESCRIPTION

Form: Compact, close internodes, vigorous rigid stems, flowers slightly above foliage, herbaceous.

Habit of growth: Some self-branching, breaks well from pinching, generally upright, yet symmetrically rounded in appearance, early flowering. Flowering plants produced from leaf cuttings with multiple shoots develop into a more mounded display.

Foliage: Simple, opposite, firm to crisp depending on environment.

(1) *Size.*—7–8 cm. wide by 11–12 cm. long.

(2) *Shape.*—Apex acute, base cordate; from oval to predominately ovate.

(3) *Texture.*—Top glabrous, underside rugose, veins green.

(4) *Margin.*—Serrated.

(5) *Color.*—Young foliage, top side yellow green 146B, red edges, under side yellow green 146C; maroon infusion on edges; mature foliage top side darker than yellow green 147A, under side yellow green 146B; maroon infusion underside and leaf edges.

(6) *Venation.*—Palmate.

FLOWERING DESCRIPTION

Flowering habits; Indeterminate, early and continuous in most environments, minimal flower drop in winter.

Natural flowering season: Indeterminate.

Flower bud description: Flat, oval, red 44A.

Flowers borne: On a sturdy raceme.

Quantity: Each raceme initially may have 4–6 flowers in blossom at one time; additional flowers will continue to develop as the previous flowers deteriorate.

Tepals:

(1) *Shape.*—Somewhat oval to nearly round.

(2) *Color.*—Top side in winter when opening more vivid than red 44A, fading to a more vivid red than 42B or 43B; under side basal tepal 42A-B, others near 43B.

(3) *Number of tepals.*—Large flowers as illustrated; 36 or more, average 16–18 tepals in lowlight to 68–70 tepals in high light.

(4) *Size of tepals.*—Basal up to 4 cm. diameter, secondary diminishing to 2 cm.

(5) *Flower size.*—Average 5–6 cm. in diameter; specimen 6–7 cm. cultivar is a sterile triploid.

DISEASE RESISTANCE

Slightly susceptible to mildew.

I claim:

1. A new and distinct cultivar of begonia named Ellen, as described and illustrated, and particularly characterized by its large flower size and compound inflorescence, brilliant and uniform red flower color, fast propagation, rapid flowering, and its foliage which is infused with maroon in margins and underside.

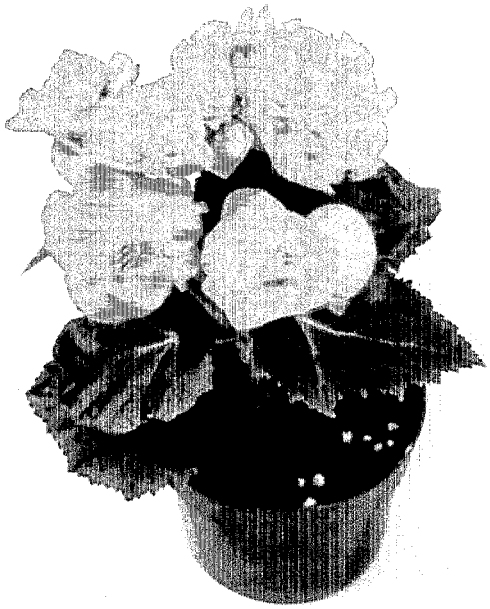

* * * * *